(12) United States Patent
Medina et al.

(10) Patent No.: US 9,399,333 B2
(45) Date of Patent: Jul. 26, 2016

(54) FORMING LAMINATED TOUCH FASTENERS

(71) Applicant: Velcro BVBA, Deinze (BE)

(72) Inventors: Isaac Soler Medina, Barcelona (ES);
James T. Grady, Chester, NH (US)

(73) Assignee: Velcro BVBA, Deinze (BE)

( * ) Notice: Subject to any disclaimer, the term of this patent is extended or adjusted under 35 U.S.C. 154(b) by 48 days.

(21) Appl. No.: 13/804,082

(22) Filed: Mar. 14, 2013

(65) Prior Publication Data

US 2013/0280474 A1    Oct. 24, 2013

Related U.S. Application Data

(60) Provisional application No. 61/635,070, filed on Apr. 18, 2012.

(51) Int. Cl.
| | |
|---|---|
| *B29C 43/28* | (2006.01) |
| *B29C 47/02* | (2006.01) |
| *B29C 47/32* | (2006.01) |
| *A44B 18/00* | (2006.01) |
| *B32B 3/06* | (2006.01) |

(Continued)

(52) U.S. Cl.
CPC .............. *B32B 3/06* (2013.01); *A44B 18/0049* (2013.01); *A44B 18/0069* (2013.01); *A61F 13/625* (2013.01); *B29C 43/222* (2013.01); *B29C 43/46* (2013.01); *B29C 47/02* (2013.01); *B29C 47/32* (2013.01); *B29C 2043/461* (2013.01); *B29C 2043/465* (2013.01); *Y10T 428/24008* (2015.01)

(58) Field of Classification Search
CPC ...... B29C 43/222; B29C 43/46; B29C 47/32; B29C 47/02; B29C 43/28; B29C 2043/465; A44B 18/0049

USPC ........ 264/244.11, 171.13, 173.1; 156/244.25, 156/244.27; 428/99, 100; 425/115; 24/450
See application file for complete search history.

(56) References Cited

U.S. PATENT DOCUMENTS

| | | | |
|---|---|---|---|
| 5,260,015 | A | 11/1993 | Kennedy et al. |
| 5,669,120 | A | 9/1997 | Wessels et al. |

(Continued)

FOREIGN PATENT DOCUMENTS

| | | | |
|---|---|---|---|
| EP | 1444079 | A1 | 8/2004 |
| EP | 1165313 | B1 | 12/2004 |

(Continued)

OTHER PUBLICATIONS

International Search Report and Written Opinion for PCT/EP2013/057494 mailed Jul. 15, 2013 (10 pages).

*Primary Examiner* — William Bell
(74) *Attorney, Agent, or Firm* — Fish & Richardson P.C.

(57) ABSTRACT

A laminated touch fastener is made in a continuous process on a mold roll. Flowable resin is pressed against the mold roll in limited areas to form projections extending from resin layers that are laminated to a flexible substrate while carried on the mold roll. In one example a continuous channel about the mold roll is positioned such that the resin at least partially fills the channel as the layers are formed, thereby forming in the channel a raised portion in which the resin layer is of a greater thickness than at a point between the projections and the raised portion. In another example, grooves in the mold roll receive ribs of a pressure applicator during forming of the layers, the ribs blocking lateral flow of the resin to form a desired edge profile.

24 Claims, 11 Drawing Sheets

(51) Int. Cl.
*B29C 43/22* (2006.01)
*A61F 13/62* (2006.01)
*B29C 43/46* (2006.01)

(56) References Cited

U.S. PATENT DOCUMENTS

| | | | |
|---|---|---|---|
| 5,851,467 A * | 12/1998 | Murasaki | 264/167 |
| 5,945,131 A * | 8/1999 | Harvey | A44B 18/0049 425/141 |
| 6,205,623 B1 | 3/2001 | Shepard et al. | |
| 6,481,063 B2 | 11/2002 | Shepard et al. | |
| 6,720,059 B2 * | 4/2004 | Fujisawa | A44B 18/0046 24/442 |
| 7,048,818 B2 | 5/2006 | Krantz et al. | |
| 7,303,711 B2 | 12/2007 | Gallant et al. | |
| 8,079,995 B2 | 12/2011 | Tachauer et al. | |
| 8,685,194 B2 | 4/2014 | Grady et al. | |
| 2001/0016245 A1 | 8/2001 | Tuman et al. | |
| 2001/0018110 A1 | 8/2001 | Tuman et al. | |
| 2002/0164449 A1 * | 11/2002 | Fujisawa et al. | 428/99 |
| 2003/0074768 A1 | 4/2003 | Shepard et al. | |
| 2003/0085485 A1 | 5/2003 | Seidel et al. | |
| 2009/0064469 A1 * | 3/2009 | Dowd | 24/452 |
| 2012/0011685 A1 * | 1/2012 | Rocha | A44B 18/0073 24/449 |
| 2012/0251790 A1 * | 10/2012 | Harhen et al. | 428/172 |

FOREIGN PATENT DOCUMENTS

| | | |
|---|---|---|
| WO | WO0050229 A1 | 8/2000 |
| WO | WO0167912 A3 | 6/2002 |
| WO | WO03039833 A1 | 5/2003 |
| WO | WO2006121695 A1 | 11/2006 |
| WO | WO2012066418 A3 | 7/2012 |

* cited by examiner

FORMING LAMINATED TOUCH FASTENERS

TECHNICAL FIELD

This invention relates to method of making laminated touch fasteners, and to products produced thereby.

BACKGROUND

Inexpensive touch fasteners, such as mechanical hook-loop fasteners, are finding wide use in a number of applications, including disposable garments and diapers. For some applications, a particularly cost-effective method of producing such fasteners is by what we call mold lamination—in which resin is applied to a carrier substrate and is simultaneously bonded or laminated directly to the substrate while an array of miniature projections are molded of the resin. An early example of mold lamination was taught by Kennedy et al. in U.S. Pat. No. 5,260,015. Later it was determined that the resin could be applied to the substrate in discrete lanes or islands, leaving at least one portion of the substrate surface exposed, rather than covering the entire surface. See, for example, U.S. Pat. Nos. 6,205,623 and 7,048,818. Because of the typical resin viscosities and projection sizes useful for many touch fastening applications, and line speeds required for cost-effective production, the required lamination/molding pressure is often quite high.

Leaving part of the substrate exposed, however, necessarily means forming an edge of the resin on the surface. In some cases the formed edges have been considered rough to the touch, or visually unappealing.

Improvements are sought in the formation of partially covered fastener laminates, and in the products produced thereby.

SUMMARY

Some aspects of the invention involve the realization that in at least some examples, undesirable roughness or visual objections can be the result of uneven lateral flow in the nip and/or substrate penetration by the resin at the resin edges, an effect exacerbated by narrower resin areas and the high pressures required to form the projections.

One aspect of the invention features a method of making a laminated touch fastener, the method including introducing flowable resin to a limited region of an outer surface of a rotating mold roll defining an array of cavities extending inward from an outer surface of the mold roll, and applying pressure to the resin to fill the cavities with resin and form a layer of the applied resin interconnecting projections molded within the cavities. The layer of resin is laminated to a flexible substrate while the layer of resin is carried on the mold roll (the substrate being of greater width than the layer of resin), thereby forming a laterally bounded layer of resin from which the molded projections extend, the bounded layer laminated to the substrate and having at least one layer edge adjacent an exposed region of the substrate, and the layer having a selvedge region void of the molded projections and defined between the projections and the layer edge. The mold roll defines a continuous channel extending about the mold roll and positioned such that the resin at least partially fills the channel, thereby forming in the channel a raised portion of the selvedge region in which the resin layer is of a greater thickness than at a point between the array and the raised portion.

In some cases the pressure is applied in a nip between the mold roll and a counter-rotating pressure roll. In some other cases, the pressure is applied in a gap between the mold roll and a non-rotating extrusion nozzle.

In some examples the layer edge is formed within the channel. In some cases the layer edge is formed by resin extending laterally beyond the channel.

The layer edge is formed, in some embodiments, against an axially distal wall defining the channel.

The channel may be defined between straight, parallel walls, for example. In another arrangement, the channel is defined between spaced walls that follow a serpentine path, such that the channel follows a serpentine path about the mold roll.

In many cases, the resin fills the channel, such that the layer of resin is molded to have a shape of the channel.

Preferably the channel has a depth, measured in a radial mold roll direction from the outer surface of the mold roll adjacent the channel, which is between about 20 and 35 percent of a width of the channel, measured along a rotational axis of the mold roll.

In some examples the channel is of constant cross-sectional area about the mold roll.

For some applications, the mold roll cavities closest to the channel are spaced from a near edge of the channel a distance less than 0.8 times a width of the channel, measured along a rotational axis of the mold roll.

The substrate may be porous, with the flowable resin pressed into pores of the substrate while the resin is carried on the mold roll. In some cases the substrate surface is fibrous and the pores are formed as spaces between substrate fibers. For some applications the substrate surface is of a topography that undulates across the surface, the layer edge traversing undulations of the surface. Such a topography may feature raised areas bounded by bonded areas, for example. The resin may be pressed into the substrate pores under the pressure applied to fill the cavities.

In some arrangements, the layer of resin is of a thickness in the raised portion that is between about two and four times a thickness of the layer at a point between the array and the raised portion.

In some examples, the channel has a bottom with a chamfered edge. In some other cases, the channel has a bottom with a rounded edge. Preferably, the channel has a depth that is less than a depth of the cavities.

In some embodiments the mold roll defines grooves immediately outboard of the channels and forming an outboard side of each channel, and ribs are disposed in the grooves during application of the pressure and impede lateral flow of the flowable resin. In some cases, the method also includes trimming flash from the grooves after the application of pressure and before laminating to the flexible substrate.

In some cases the method also includes, after the application of pressure and before laminating to the flexible substrate, applying heat to an exposed surface of the resin layer while the resin layer is carried on the mold roll.

Another aspect of the invention features a touch fastener product having a flexible, sheet-form substrate having a broad surface, a layer of resin directly laminated to the broad surface, and an array of discrete fastener projections extending from the layer of resin. The layer of resin covers only a portion of the broad surface and defines a layer edge adjacent an exposed region of the broad surface, and the layer of resin is of a greater thickness at the layer edge than at a point between the array and the layer edge.

In some examples the layer edge features a rib, and the layer defines a selvedge area extending from the fastener projection array to the rib, the selvedge area being of a thickness less than a thickness of the resin layer at the rib. The rib is preferably shorter than the fastener elements. In some cases, the rib has a rounded outer edge. For some applications, the rib has a height, measured from the resin layer in the selvedge area, that is between about 20 and 35 percent of a width of the rib.

In some examples, the substrate is longitudinally continuous and the layer of resin forms a discrete band of resin running along a length of the substrate.

In some cases the layer of resin covers only a bounded area of the broad substrate surface and is surrounded by the exposed region of the broad surface. The layer edge features a rib extending about a periphery of the resin layer.

Another aspect of the invention features a method of making a laminated touch fastener, the method including introducing flowable resin to a limited circumferential band of an outer surface of a rotating mold roll defining an array of cavities extending inward from an outer surface of the mold roll within the band, and defining grooves on either side of the circumferential band. The mold roll is positioned in cooperation with a pressure applicator, with ribs of the pressure applicator positioned in the grooves of the rotating mold roll to laterally bound the circumferential band. With the ribs positioned in the groove, pressure is applied to the resin to fill the cavities with resin and form a layer of the applied resin interconnecting projections molded within the cavities and extending across the circumferential band between the ribs. The layer of resin is carried on the mold roll to a position in the rotation of the mold roll where the grooves are free of the ribs, and then the layer of resin is laminated to a flexible substrate while the layer of resin is carried on the mold roll. The substrate is of greater width than the layer of resin, and a laterally bounded layer of resin is formed, from which the molded projections extend, the bounded layer laminated to the substrate and having at least one layer edge adjacent an exposed region of the substrate.

In some examples the method also includes trimming flash from the grooves after the application of pressure and before laminating to the flexible substrate.

Some examples also feature, after the application of pressure and before laminating to the flexible substrate, applying heat to an exposed surface of the resin layer while the resin layer is carried on the mold roll.

Various implementations of the inventive concepts presented herein can be useful in enabling the formation of more visually and tactilely pleasing fastener laminates, even when forming projections under very high nip pressures very close to the resin edges. Dimensional variability in widths of fastening lanes or deposits may also be reduced.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
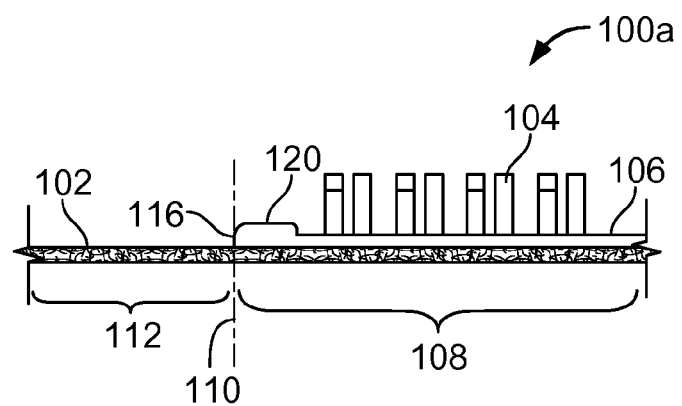
FIG. 1 is a partial end view of a touch fastener laminate.
Figure 2:
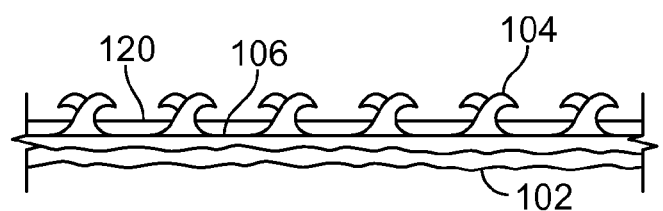
FIG. 2 is a side view of the touch fastener of FIG. 1
Figure 3:
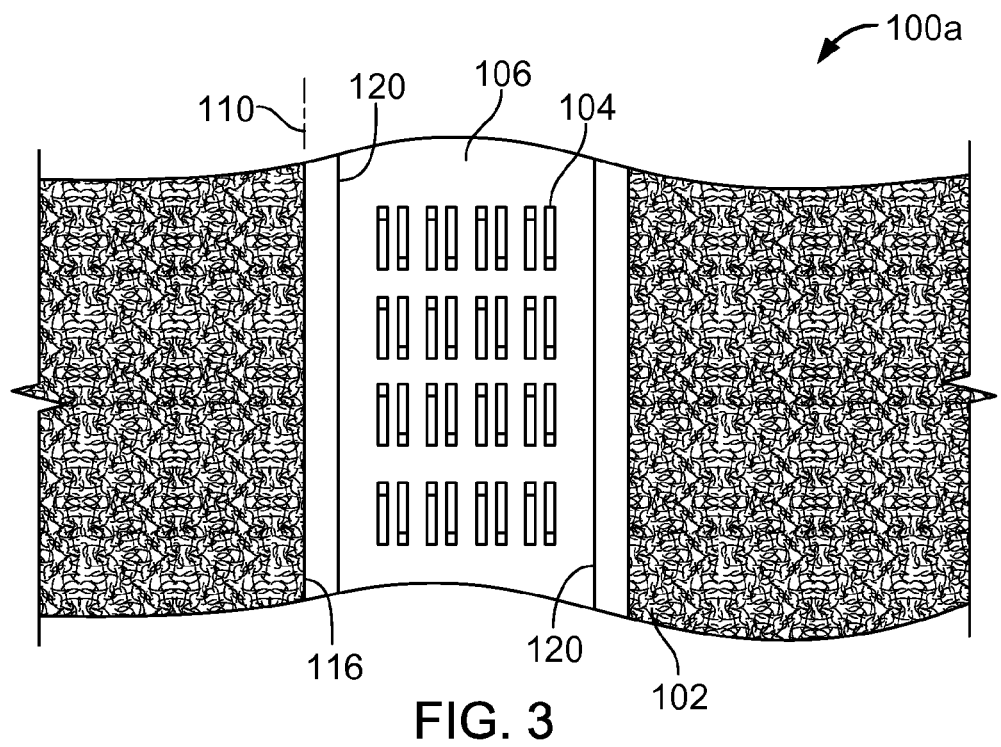
FIG. 3 is a partial top view of the touch fastener of FIG. 1, showing one of multiple strips of resin on a substrate surface.

Referring first to FIGS. 1-3, touch fastener 100*a* includes a flexible substrate 102 and a plurality of defined structures 104. Structures 104 (such as molded fastener elements) extend from a solidified base layer 106 of flowable resin (e.g., polypropylene, polyethylene, or any other suitable resinous material) supported by the substrate surface within a first region 108 of the substrate. A dividing line 110 represents a boundary between first region 108 and an adjacent second region 112. In this example, substrate 102 is a non-woven, fibrous web of a particular porosity that varies locally across the substrate surface. Substrate 102 may be, for example, what is known in the non-woven industry as a staple fiber non-woven, a needle-punched non-woven, a spunbonded web such as a point un-bonded web, a spunbonded/meltdown/spunbonded (SMS) web, etc. Alternatively, substrate 102 may be a textile product such as a knit or woven product. Besides porosity, other surface characteristics may also vary across the surface of substrate 102, such as the local height of the surface. Such substrate surfaces may have a topography that undulates across the surface, and the layer edge may traverse undulations of the surface. Some substrates, for example, are embossed to form a desired surface topography.

As described above, structures 104 extend from base layer 106. In this example, base layer 106 has a relatively straight edge 116 having little or no splay. Edge 116 is disposed on the substrate surface within first region 108 and adjacent an exposed portion of the first region, as discussed in greater detail below. As shown, structures 104 are formed as J-hooks defining a crook for snagging fibers of looped material. Structures 104, however, can be formed having other suitable shapes or sizes. Referring specifically to FIG. 3, structures 104 are positioned in a patterned configuration on base layer 106, which may be in the form of spaced parallel lanes extending along substrate 102. Only one strip is shown in these figures. In some examples, the parallel lanes are approximately 15 millimeters wide, run down the length of substrate 102, and are positioned approximately 15 millimeters from the outboard edges of the substrate. Such configurations and arrangements may be especially advantageous in certain implementations (e.g., for forming precursor materials for making diaper tabs—see FIG. 18A). However, as discussed below, other suitable configurations or arrangements of base layers 106 and/or structures 104 are also envisioned (see FIG. 4, for example).

The edges 116 of each strip of base layer 106 feature a raised lip 120, in which the thickness of the base layer is greater than in a region between the lip and the array of structures 104. By thickness we mean the measurement of the base layer in the direction perpendicular to the plane of the substrate, as measured from a reference datum corresponding essentially to the upper surface of the substrate. In the examples shown and discussed below, the base layer between the edge lips 120 and surrounding the structures is generally of a constant nominal thickness, from which the structures 104 can be considered discrete, local extensions formed of the same resin as the base layer. In this example, lips 120 bound the edges of each strip of base layer 106, an outer edge of the lip being coextensive with, and forming, the distal edge of the base layer strip. In this instance, lips 120 are of generally constant width, as measured across the strip, have a relatively flat upper surface lower than the engageable heads of the fastener elements 104, and are wider than an individual fastener element.

Figure 4:
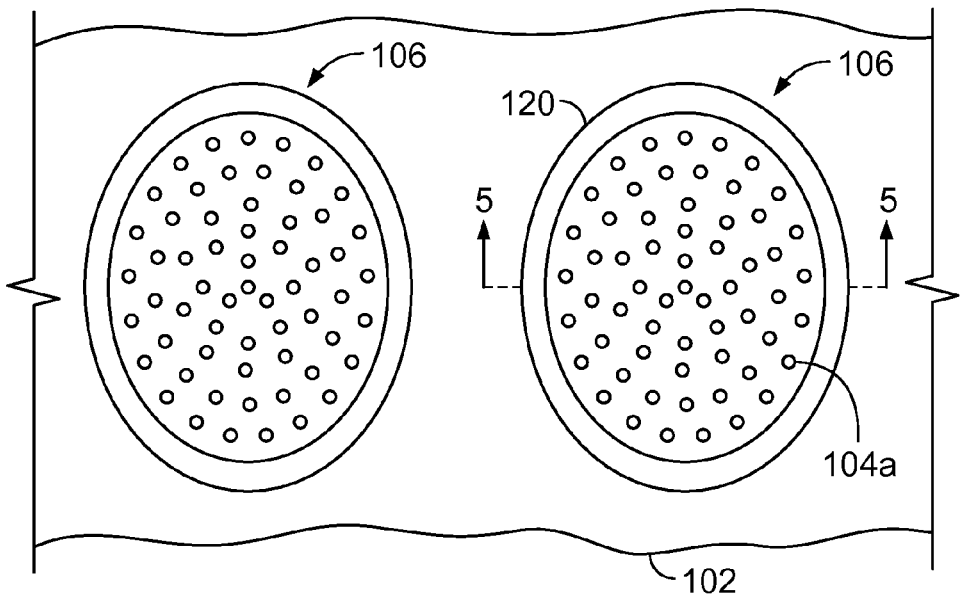
FIG. 4 is a partial top view of a second touch fastener, having islands of resin on a substrate surface.
Figure 5:
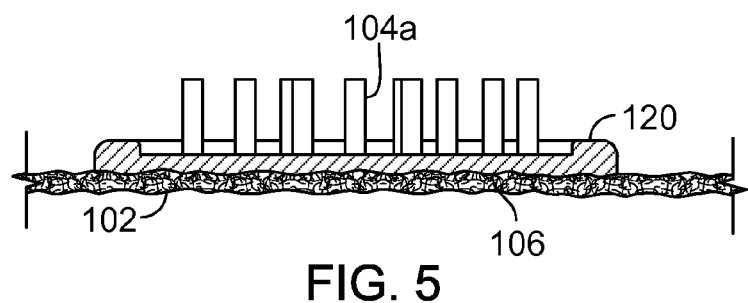
FIG. 5 is a cross-sectional view of FIG. 4, taken along line 5-5.

The Referring next to FIGS. 4 and 5, the regions of substrate covered by the resin base layer need not be straight strips. In this example, base layer 106 is in the form of oval patches, each having a raised lip 120 defining its perimeter. Structures 104a are in the form of discrete stems of molded resin, rising vertically from the base layer. From such stems fastener elements may later be formed by deforming distal ends of each stem to form an overhanging head or cap (not shown in these views). The stems need not be arranged in straight rows or columns, but may be arranged in other patterns, preferably with a spacing that allows separate engageable heads to be formed. Exposed surface of substrate 102 surrounds each oval patch, such that each patch can be considered an island of resin covering and permanently laminated to the substrate surface. As illustrated in FIGS. 2 and 5, the base layer of resin preferably only penetrates the substrate to a limited depth, such that an opposite side of the substrate remains free of the resin of the base layer. The opposite side of the substrate may feature loops or other fibers engageable by the structures of the base layers when the touch fastener is wrapped about an object.

Figure 6:
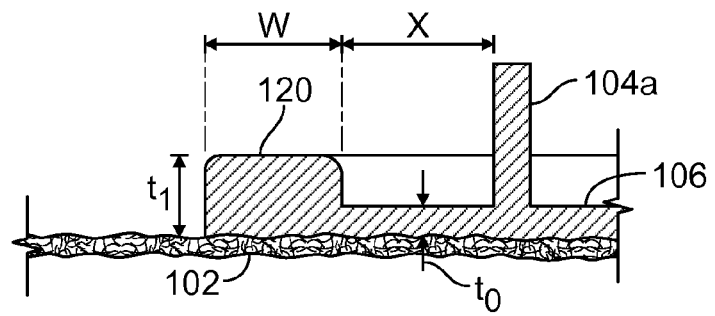
FIG. 6 is an enlarged cross-sectional view of the edge of the resin island shown in FIG. 5.

Referring to FIG. 6, lip 120 has a thickness, $t_1$, which is greater than nominal base layer thickness $t_0$ as measured between the lip and the nearest functional structure 104a. Preferably, the thickness $t_1$ in the lip that is between about two and four times nominal base layer thickness $t_0$, or any thickness of the base layer between the array of structures 104a and the lip. In this example, the thickness difference $(t_1-t_0)$ is about 0.0065 inch (0.16 mm), and the width 'W' of the lip is about 0.036 inch (0.91 mm). The inner edge of the lip is spaced from the closest surface of the nearest stem 104a by a distance 'X' of about 0.12 inch (0.3 mm). Because of the resin pressures required to properly mold stems 104a (or the fastener elements 104 of FIG. 3), separation distance 'X' is preferably at least 0.2 mm, and for many applications is in the range of 0.2 to 0.4 mm. In some cases, the stems 104a or fastener elements are molded with stiffening side ribs facing edge lip 120, in which case the spacing distance 'X' is measured from the nearest stiffening rib surface. Lip 120 has an aspect ratio, defined as the ratio of the width W to the thickness difference $(t_1-t_0)$, which is preferably in the range of 2 to 5. Other lip configurations are described below.

Figure 7:
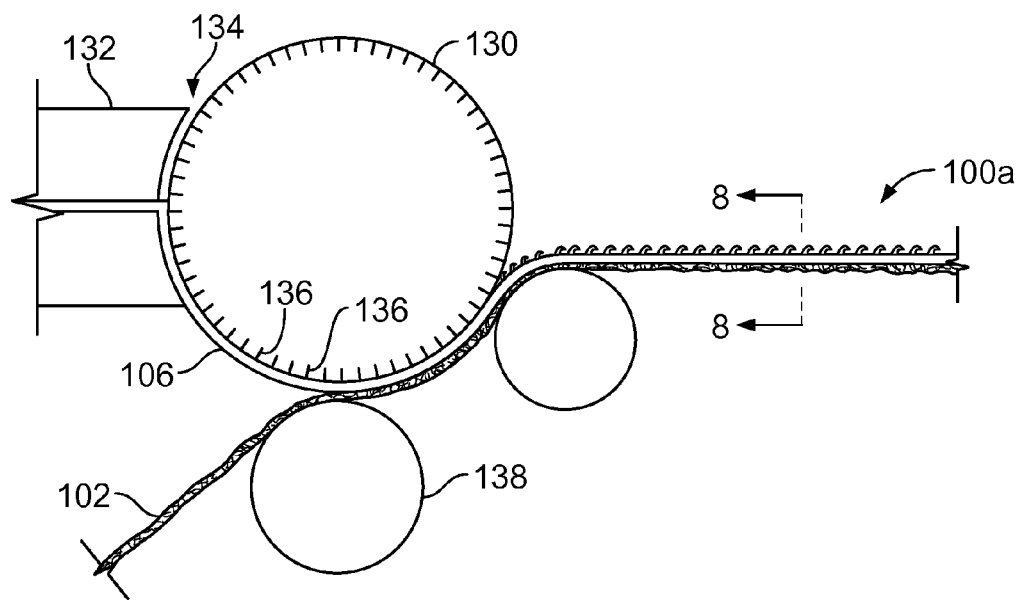
FIG. 7 shows a first apparatus and method of making a touch fastener.

Referring next to FIG. 7, one method of making a touch fastener 100a features the continuous molding of the base layers and associated structures on a rotating mold roll 130, against which resin is extruded under pressure by an extrusion nozzle 132 shaped to define a narrow gap 134 between the nozzle and the mold roll. The basic configuration of such an apparatus is taught in U.S. Pat. No. 5,669,120, the entire contents of which are hereby incorporated by reference. Into this gap 134 resin is extruded under pressure, and the pressure forces the resin into discrete molding cavities 136 defined in the surface of the mold roll. In this example, cavities 136 are shaped to form fastener elements 104 having overhanging heads. In some other examples, only stems are formed. In either case, resin remaining on the surface of mold roll 130 forms the base layer 106 of resin, which is then laminated under pressure, in a nip between mold roll 130 and a counter-rotating pressure roll 138, while the base layer is still carried on the mold roll and sufficiently molten to partially embed in the surface of substrate 102 without the use of added adhesives. Following lamination, the finished touch fastener 100a is stripped from the mold roll and spooled for later use.

Figure 8:
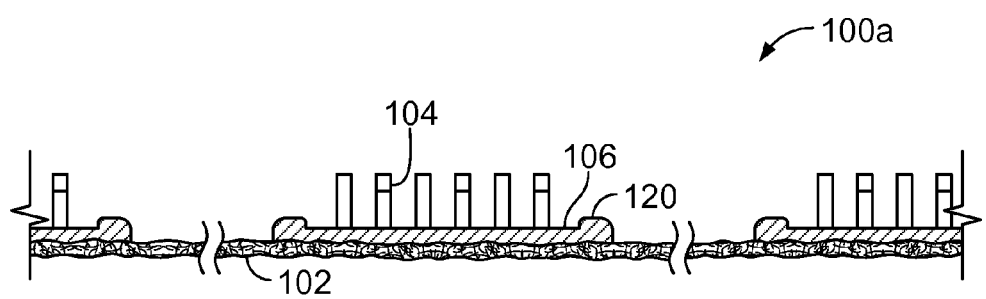
FIG. 8 is a cross-sectional view of FIG. 7, taken along line 8-8.
Figure 9:
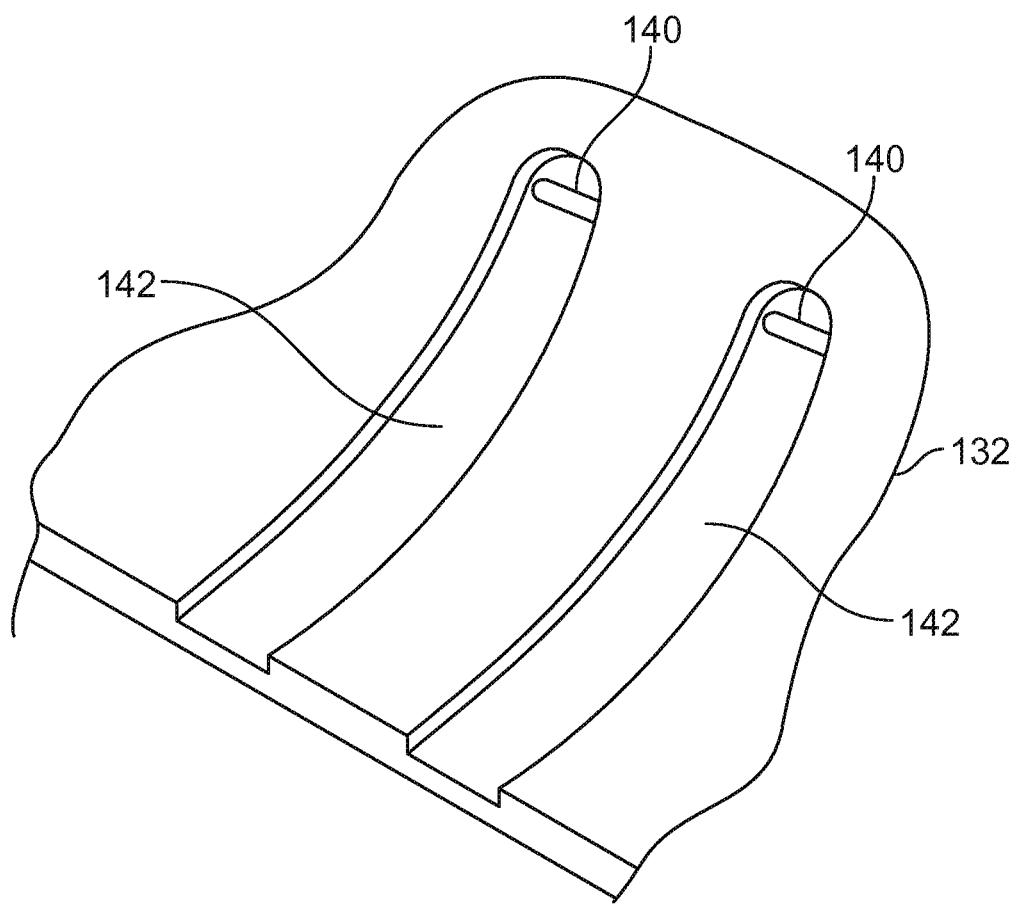
FIG. 9 is a partial perspective view of the face of the extruder of FIG. 7.

As shown in FIG. 8, the resin is applied to the mold roll in discrete strips, such that the base layer 106 is formed in spaced strips or bands on substrate 102, leaving intermediate bands of the substrate surface free of the resin. Circumferential grooves defined in the surface of the mold roll mold lips 120 at the edges of each strip. Referring also to FIG. 9, resin is extruded into the mold roll surface in discrete streams by the extruder, such as through discrete die orifices 140 spaced along the axis of the mold roll. The face of the extruder defines an associated channel 142 extending from each orifice 140 to the downstream edge of the extruder face. The side walls defining the channel help to constrain the extruded resin laterally as pressure in the extrusion gap forces the resin into the mold roll cavities and channels.

Figure 10:
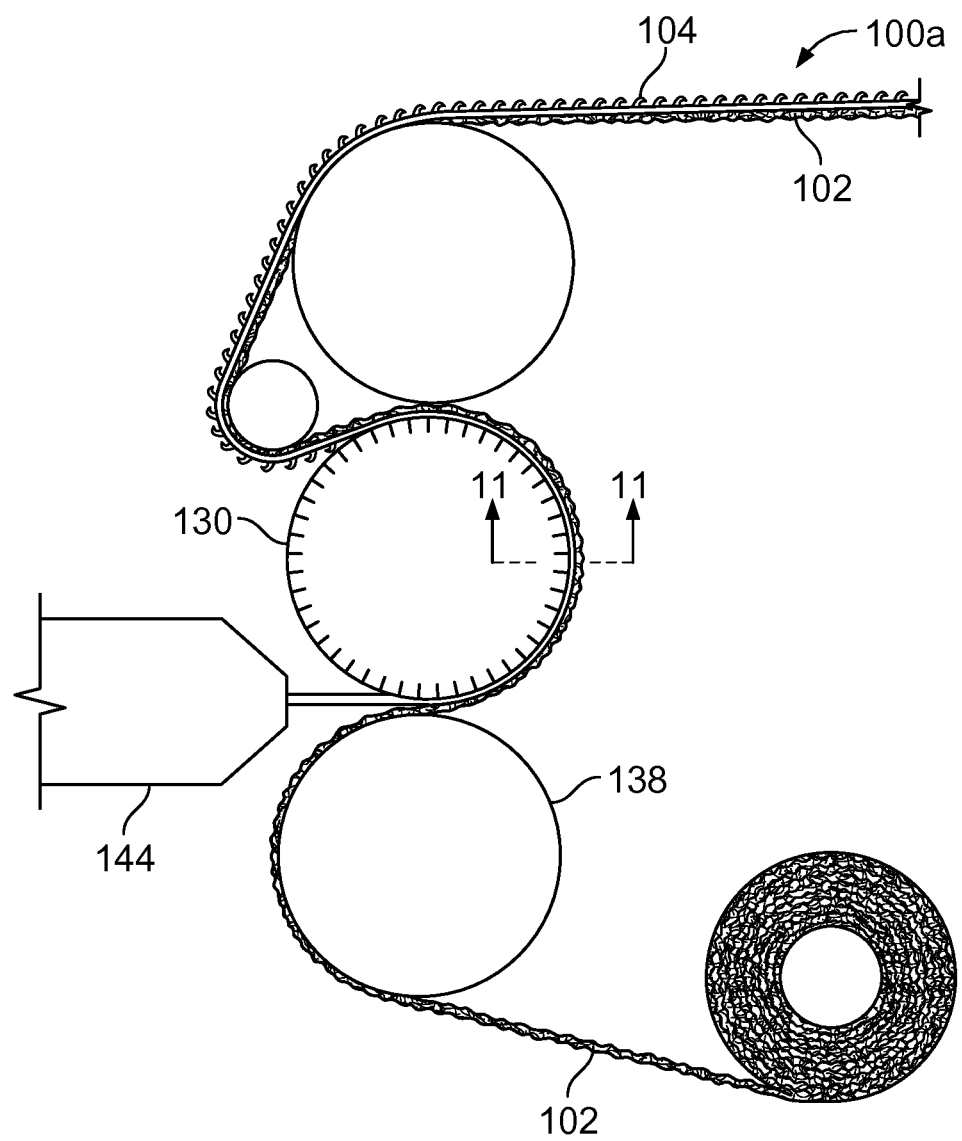
FIG. 10 shows a second apparatus and method of making a touch fastener.

Referring next to FIG. 10, another method of making the touch fastener features extruding molten resin directly into a nip between mold roll 130 and a smooth, counter-rotating roller 138 about which substrate 102 is trained, such that the substrate and resin enter the nip together, and nip pressure forces the resin into the mold roll cavities and channels while directly laminating the base layer of resin to the substrate, with some of the resin penetrating interstices in the substrate surface to permanently secure the resin. In this example, extruder 144 is positioned to be aligned with the nip, and features a deckled die orifice that forms multiple, spaced apart strips of resin that each form a continuous drape into the nip, such that the resin contacts the substrate surface just prior to being subjected to high nip pressure. In another arrangement (not illustrated), the extruder extrudes directly onto the substrate surface (e.g., by extruding downward onto the surface) upstream of the molding nip. In either arrangement, the substrate and moldable resin enter the nip together, and the same pressure that forces the resin into the mold cavities also forces the resin into the substrate. After traveling about the mold roll, the formed structures (e.g., fastening elements) are pulled from their cavities and the finished touch fastener product is split and/or spooled for later use. In some embodiments, the mold roll cavities form straight, non-overhanging stems that are later deformed to form engageable structures, such as by passing the molded stems under or against a heated roller or plate (not shown).

Figure 11:
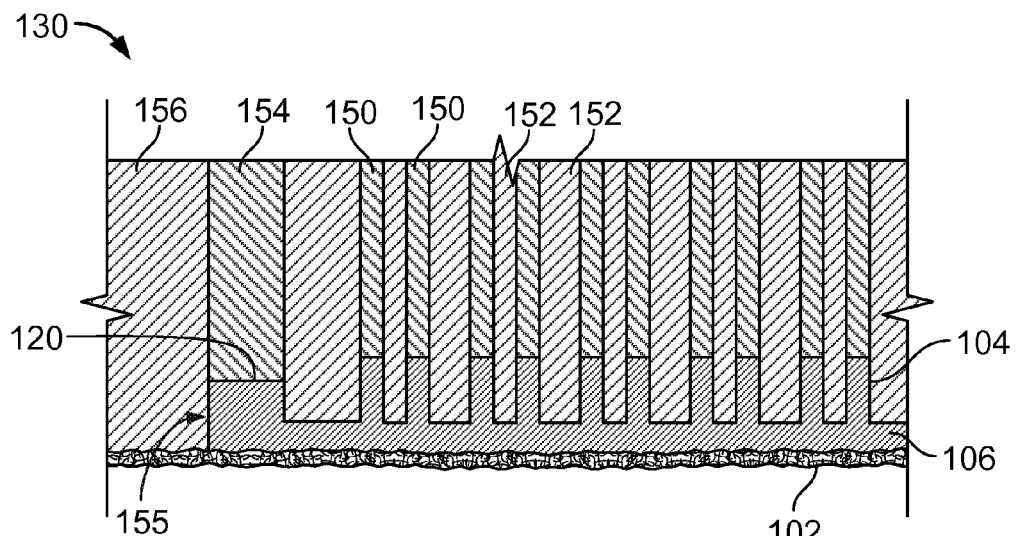
FIG. 11 is a cross-sectional view of FIG. 10, taken along line 11-11.

As shown in FIG. 11, mold roll 130 (whether as employed in the method illustrated in FIG. 10 or in FIG. 7) is constructed as an axially compressed stack of flat, circular plates or rings. Mold rings 150, which have a profiled circumference shaped to define the longitudinal profiles of the structures 104 (e.g., J-hooks, stems or palm-tree hooks) to be molded, are sandwiched between spacer rings 152 that have a continuous, circular outer surface of constant diameter matching the diameter of the mold rings between the cavities. Each mold ring forms a corresponding longitudinal row of structures, and the thickness of the spacer rings defines the distance between the rows. As shown, some spacer rings 152 may be thicker than others, to produce the desired row spacing. A lip ring 154 of reduced diameter as compared to the spacer rings 152 is positioned to form the lip 120 at the edge of the base layer strip, and defines the base of the channel 155 in which the lip is formed. To form a lip of the preferred aspect ratio, the lip channel has a depth, measured radially from the outer surface of the mold roll adjacent the channel, that is between about 20 and 35 percent of the width of the channel, measured along the rotational axis of the mold roll. A relatively thick spacer ring (or stack of thinner spacer rings) is positioned between the lip ring 154 and the closest mold ring 150, of a thickness selected to form the region between the lip and the array of molded structures. For some applications this spacer ring is selected to be of a thickness such that the mold roll cavities closest to the lip-forming channel are spaced from a near edge of the channel a distance less than 0.8 times a width of the channel, measured along the rotational axis of the mold roll. Or to state this another way, the channel width is in some cases over 1.2 times a distance from the channel to the nearest mold roll cavities. Some separation of the channel from the cavities is needed to maintain sufficient pressure at the adjacent cavities, for proper projection formation. We have found, for example, that when molding typically dense arrays of small fastener elements of polypropylene suitable for disposable diapers and the like, in which the fastener elements are only of a height of about 0.015 inch (0.4 mm), a distance of at least 0.008 inch (0.2 mm) was sufficient to fill the closest mold cavities.

This set of rings, including mold and spacer rings sandwiched between two lip rings, forms a ring set for forming one molded strip along the substrate, and is axially aligned with one flow of resin from the extruder. Each ring set is spaced from other ring sets by a relatively thick, cylindrical ring 156 or set of rings. Ring 156 may be of slightly larger diameter than the nominal mold ring diameter, to provide higher compression of the substrate and impede lateral resin flow beyond the lip channel.

To mold structures of a size appropriate for engaging loops in a touch fastener, for example, the mold rings 150 are relatively thin. In one example, each mold ring 150 of a nominally 10 inch (25 cm) diameter mold roll has a thickness of only about 0.004 to 0.008 inch (0.10 to 0.20 mm). Filling such narrow cavities with resin of properties suitable for forming strong fastener hooks at commercial molding speeds requires significant nip pressures that act in all directions. When the entire length of the nip is used for molding, such as when covering an entire substrate surface with fastener elements, molding inconsistencies caused by nip pressure variations near the edges of the substrate can be removed by trimming the substrate edges after molding. Away from the edges, the resin is generally constrained by the adjacent resin to flow up into the cavities, and down into the substrate. Shear effects caused by the rotation of the rolls can cause some longitudinal displacement, but far from the resin edges there is relatively little lateral resin flow. When forming narrow strips of molded base layer under such high pressures, there is some lateral widening of the strip of resin in the nip. The amount of widening tends to vary due to variations in the surface of the substrate, local pressure fluctuations, etc. This can result in a visually unappealing lack of straightness at the edge of the molded strip.

By providing a lip-forming channel on the mold roll, positioned to correspond to the edge of the molded strip, we have found that we can accommodate some of that pressure fluctuation, and improve the straightness of the strip edge as molded. In some sense, it is believed that the lip-forming channel acts as a sort of lateral resin accumulator, across which the nip pressure drops more precipitously during nip molding than in cases where no such channel is provided. This can improve the straightness of the molded edge, whether or not the lip channel is completely filled, and even if some small amount of resin extends past the lip channel.

Figure 12:
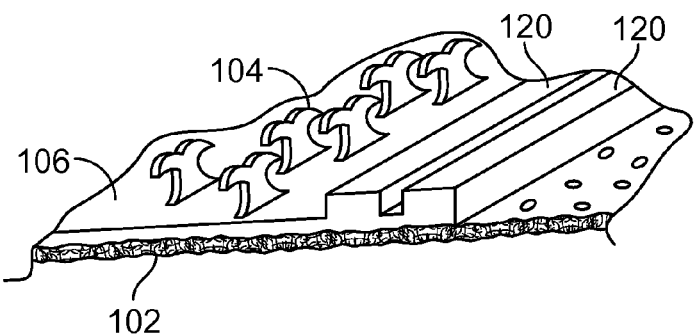
FIG. 12 is an enlarged perspective view of an edge of a resin strip having twin lips.
Figure 13:
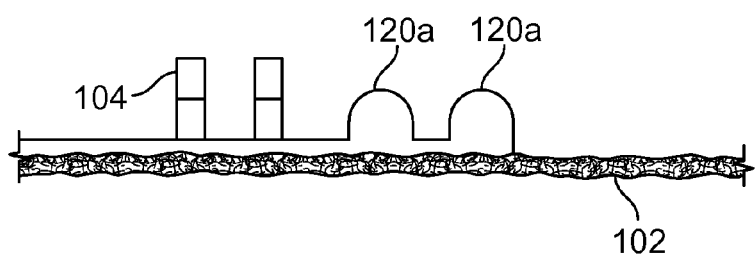
FIG. 13 is an enlarged end view of another resin strip edge.
Figure 14:
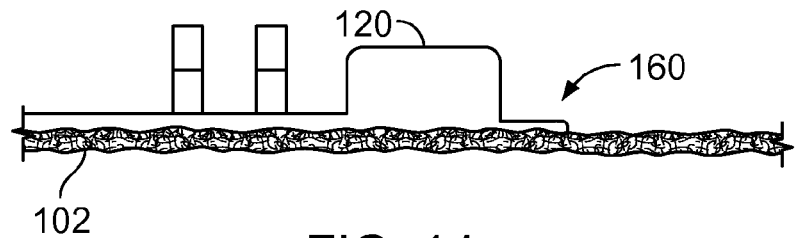
FIGS. 14 and 14A are end and perspective views of a resin strip edge having some resin overflow.
Figure 14A:
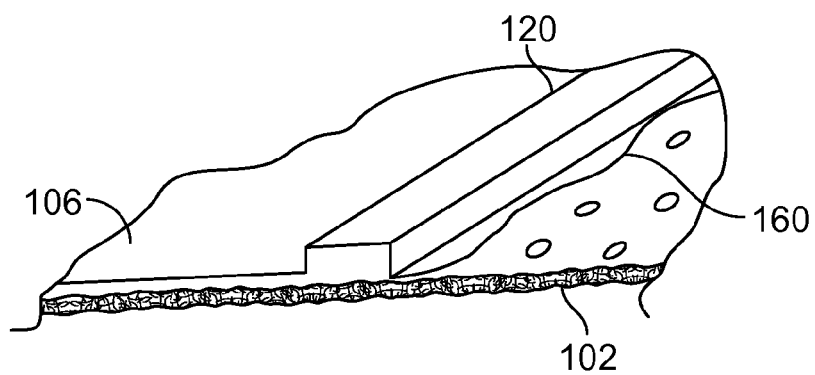
Figure 15:
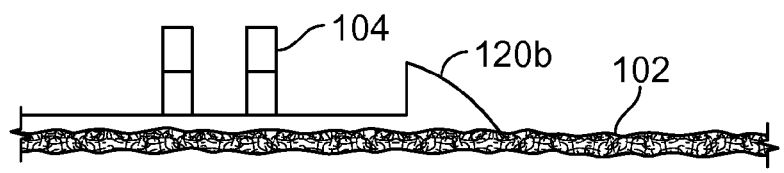
FIGS. 15 and 15A are end and perspective views of a resin strip edge with a lip formed in a partially filled channel.
Figure 15A:
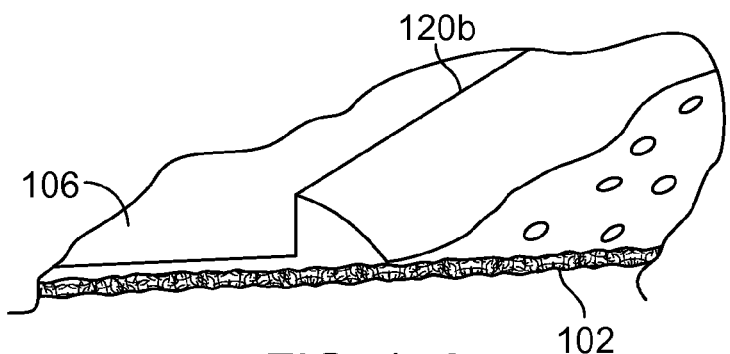

FIGS. 12-15A illustrate a number of examples of strip edge configurations with edge-straightening lip formations. In the example of FIG. 12, the strip edge has been molded to have a pair of lips 120, separated by a region of relatively thinner resin. Each rib 120 was molded to be 0.036 inch (0.9 mm) wide, and were separated by a spacing of 0.008 inch (0.2 mm). In some cases, two lips may facilitate a smooth transition from free substrate to hook strip, to make the resin edge softer or give the perception of softness. Resin extending into the outer rib channel may be more readily detected during manufacture, allowing for better quality control and finer process adjustment. Similarly, the strip edge shown in FIG. 13 features two spaced lips 120a, but with radiused upper edges for a softer feel. Alternatively, the upper edges may be chamfered. The inner lip is also illustrated as narrower than the outer lip, to show that the lips need not be of equal thickness. In some cases, the lip closest to the fastener elements is wider than the outer lip. Similarly, the lips need not be of equal height, but for most applications the lips are preferably shorter than the functional fastener element structures 104. The strip edge shown in FIGS. 14 and 14A features some lateral overflow 160 beyond lip 120. While the overflow has some visual lateral fluctuation (as shown in FIG. 14A), the overall straightness of the resin edge is improved as compared to a similar strip formed without lip 120. FIGS. 15 and 15A show a strip edge formed on a mold roll with the same lip channel as formed the lip shown in FIG. 14, but that was not completely filled with resin during nip molding. As a result, the thickness of lip 120b varies across its width, and the lip has a free-formed upper surface. The resin edge produced in this example has some visible fluctuation along its length, but is again straighter than would be produced without forming lip 120b.

Figure 16A:
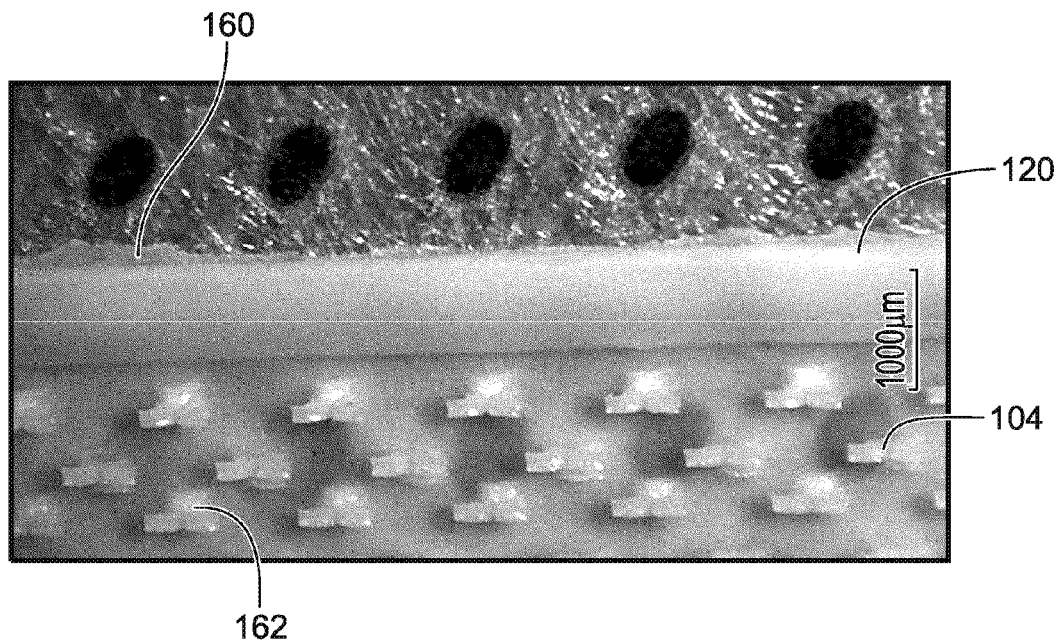
FIGS. 16A and 16B are top and end views, respectively, of a first sample product.
Figure 16B:
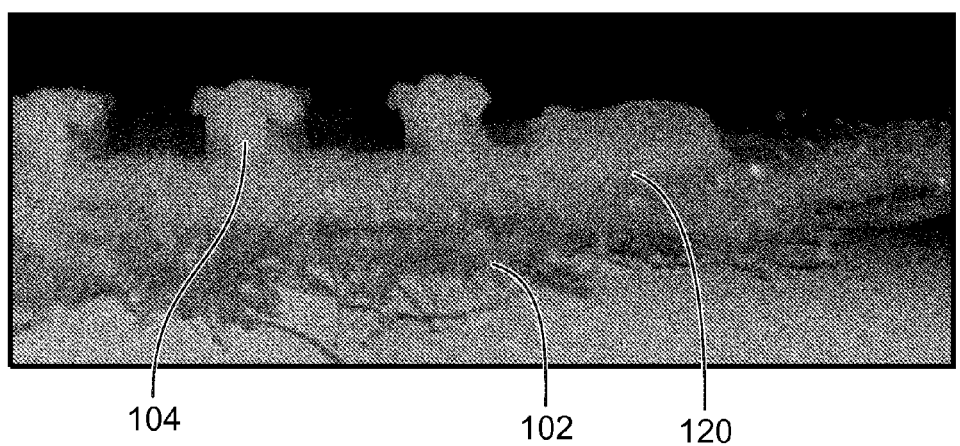

The photographs of FIGS. 16A and 16B show enlarged views of a strip edge molded to have a lip 120 as discussed above. In this example, small amounts of resin overflow 160 beyond the far edge of the lip are visible. Also visible in this example are molded reinforcing ribs 162 formed on the side of each fastener element 104, facing rib 120. This particular resin strip was formed of polypropylene on a non-woven SMS substrate of a basis weight of 60 grams per square meter. The molded palm-tree hooks were 0.015 inch (0.38 mm) tall and were 0.006 inch (0.15) mm thick. In an attempt to form this product with only a 0.3 mm thick spacer ring between the last row of fastener elements and the rib, the pressure reduction across the rib prevented the complete filling of the nearest row of fastener elements.

Figure 17A:
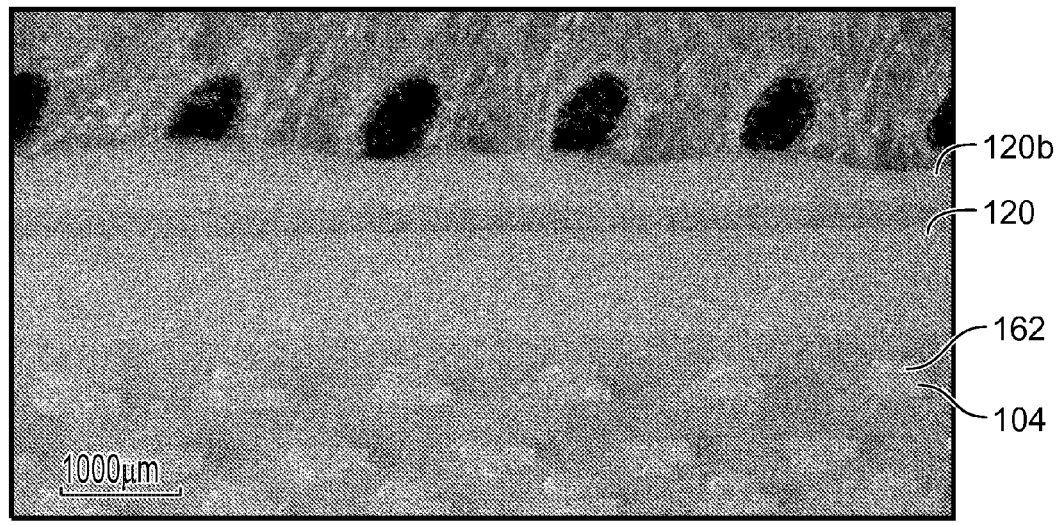
FIGS. 17A and 17B are top and end views, respectively, of a second sample product.
Figure 17B:
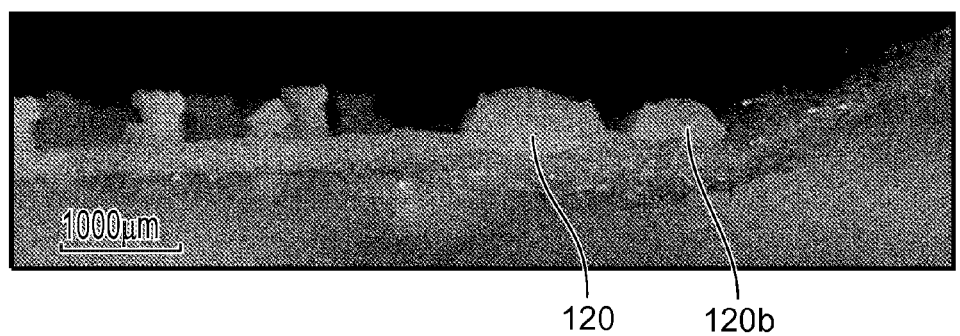

In the example shown in FIGS. 17A and 17B, an inner rib channel essentially filled during nip molding, forming inner rib 120, while an outer rib channel only partially filled, forming outer rib 120b. As can be seen in FIG. 17A, outer rib 120b forms the longitudinal edge of the resin strip, and has some width fluctuation. The pressure-diminishing effect of the rib channels is also evident from the change in thickness of the substrate seen in FIG. 17B. In areas of highest nip pressure, on the left side of the photograph, the resin has more deeply impregnated the substrate and the substrate is more crushed than under the edge ribs. This example was also formed of polypropylene resin and 60 gsm SMS non-woven material.

The cross-sectional size of lip channel needed to improve edge straightness will vary from application to application. It is believed that the higher the substrate porosity, the less lip channel volume will be required, for example. Similarly, for higher viscosity resins, or for thinner substrates, less lip channel volume may be necessary.

Figure 18A:
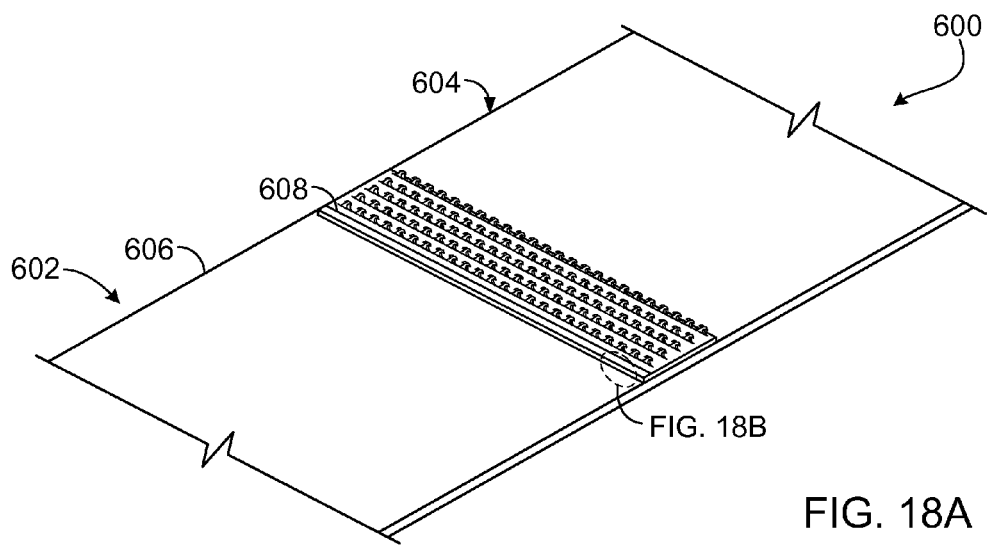
FIG. 18A is a perspective view of a diaper tab.
Figure 18B:
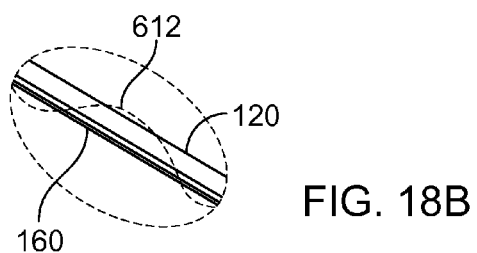
FIG. 18B is an enlarged view of area 18B in FIG. 18A.

Referring next to FIG. 18A, diaper 600 including a diaper chassis 602 (for clarity, the diaper chassis is not shown in detail or in its entirety) and a diaper tab 604 extending from the chassis and featuring a lane of loop-engageable structures. More specifically, diaper tab 604 includes a substrate 606 (such as a stretchable non-woven material) having a base layer of resinous material 608 laminated to its surface. Loop engageable structures (e.g., capped stems or hooks) extend from base layer 608. Diaper tab 604 can be made according to any method or system described above. As illustrated in the enlarged view of FIG. 18B, the variation of edge 160 is significantly less than it would have been had lip 120 not been formed (indicated for purposes of illustration as dashed line 612).

Another method of improving resin edge straightness in the formation of touch fastener regions on a substrate, particularly a substrate with a varying surface characteristic, is taught in pending U.S. patent application Ser. No. 13/236,415, the entire contents of which are incorporated herein by reference. The methods taught in that application are not incompatible with the methods taught above, and may be employed in combination.

Figure 19:
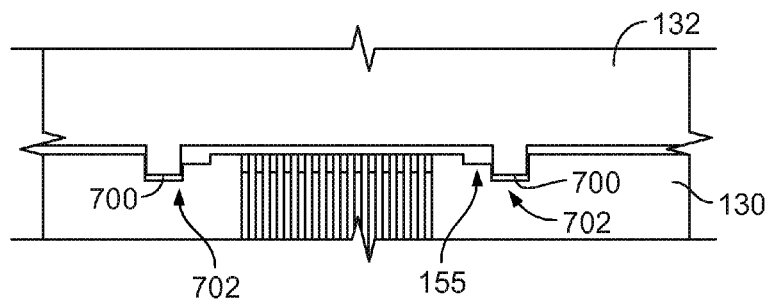
FIG. 19 is a partial cross-sectional view of a molding gap between a mold roll and a keyed injection head.
Figure 20:
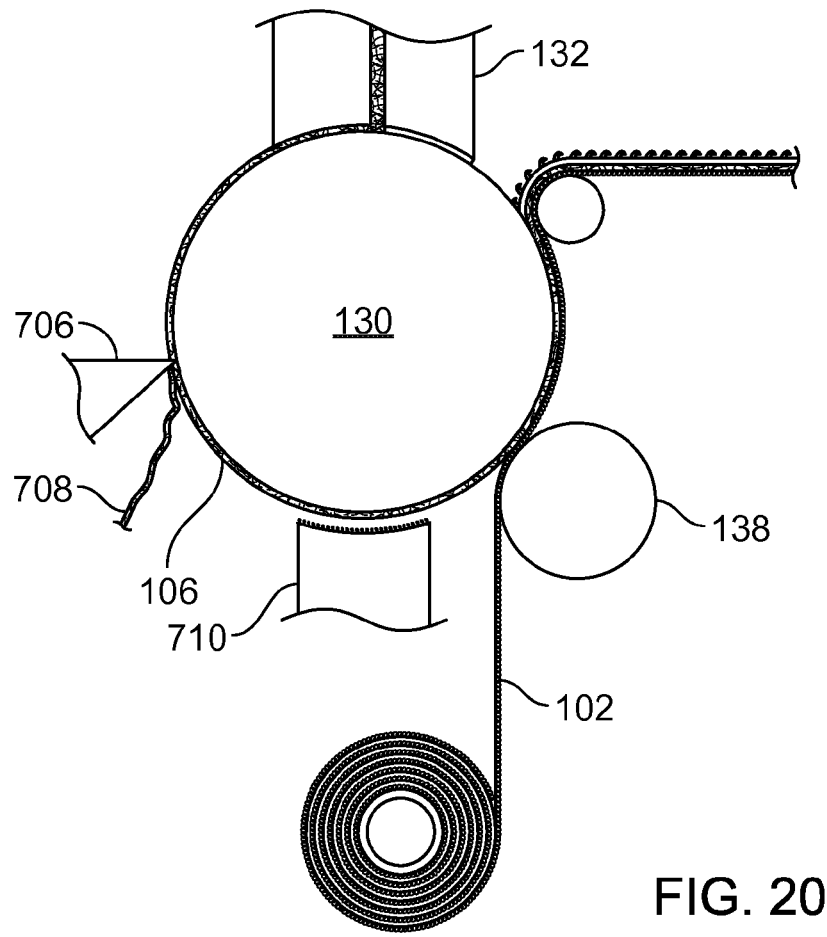
FIG. 20 illustrates another method and apparatus for making a laminate touch fastener.

The edge channel concepts discussed above may be combined with other molding apparatus features and methods, to achieve desired edge properties. For example, referring next to FIG. 19, the method and apparatus of FIG. 7 may be modified to include a keying of the surface of nozzle 132 to mold roll 130. In this example, the surface of nozzle 132 features ribs 700 received in grooves 702 extending about the mold roll just outside of the channels 155 in which the lips are formed. In this instance, inner side walls of ribs 700 form the outer sides of channels 155, as flow barriers that form the edges of the molded resin lane. Grooves 702 can be formed by stacking rings of desired diameters and thicknesses, as discussed above with respect to FIG. 11, or the outer diameters of thick mold plates can be turned to create the desired grooves 702 and channels 155 within the width of a single mold plate. Referring also to FIG. 20, any flash that forms within the mold roll grooves 702 may be trimmed away while the resin is still cooling on the mold roll, by a set of blades 706 that extend into the grooves and scrape at least against the inner walls of the grooves. The removed flash 708 is then guided away from the mold roll and recycled. The trimmed lanes of resin may then pass over a radiant heater 710, to soften the exposed, back surfaces of the base layer 106 just prior to introduction of substrate 102, which is laminated under nip pressure to the softened or slightly melted resin surfaces while still carried on mold roll 130. In this manner, very precise fastener lane edges may be formed on the laminate.

The keying concept described above with respect to FIG. 19 may also be employed to key a mold roll and pressure roll, as a variation of the method and apparatus featured in FIG. 10. In such an example, trimming may occur just downstream of the molding nip, prior to introduction of the substrate in a further nip against the mold roll. Furthermore, the keying concept may be employed, either with an extrusion nozzle or a molding nip, separate from the edge rib formation concepts discussed above. In other words, another variation of the mold gap arrangement shown in FIG. 19 does not include any rib-forming channels 155 but otherwise appears as shown.

Figure 21:
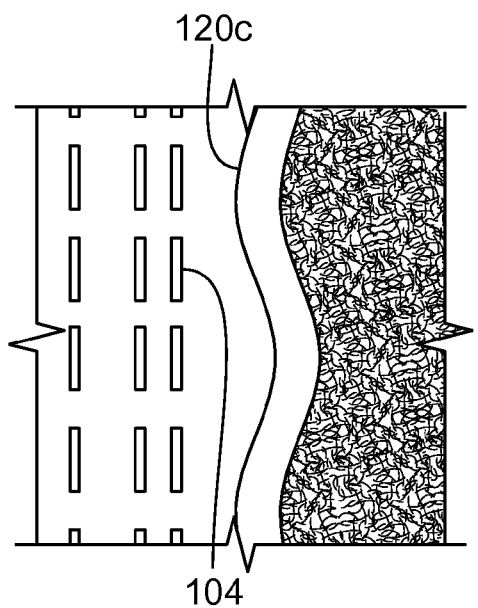
FIG. 21 shows a portion of an edge of a resin lane, in top view, with a sinusoidal profile.

While the examples of longitudinal edge ribs discussed above have generally been illustrated as being linear, with straight side walls, in some situations it may be desirable to form a longitudinal edge rib that follows a desired, non-linear path. For example, FIG. 21 illustrates an edge rib 120c formed in a molding channel that follows a sinusoidal or otherwise serpentine path, such that the distance between the rib and the molded fastener elements undulates along the length of the laminate. Such undulation may induce locally longitudinal flow of the resin under molding pressure, into those regions where the rib is farther from the fastener elements. Such an undulating rib may be considered preferable over a perfectly straight edge, for example, in some personal care products. Formation of the rib aids in achieving such a desired edge pattern from a generally constant extrusion of resin.

While a number of examples have been described for illustration purposes, the foregoing description is not intended to limit the scope of the invention, which is defined by the scope of the appended claims. There are and will be other examples and modifications within the scope of the following claims.

What is claimed is:

1. A method of making a laminated touch fastener, the method comprising:
   introducing flowable resin to a limited region of an outer surface of a rotating mold roll defining an array of cavities extending inward from an outer surface of the mold roll;
   applying pressure to the resin to fill the cavities with resin and form a layer of the applied resin interconnecting projections molded within the cavities; and
   laminating the layer of resin to a flexible substrate while the layer of resin is carried on the mold roll, the substrate being of greater width than the layer of resin, thereby forming a laterally bounded layer of resin from which the molded projections extend, the bounded layer laminated to the substrate and having at least one layer edge adjacent an exposed region of the substrate, the layer having a selvedge region void of the molded projections and defined between the projections and the layer edge;
   wherein the mold roll defines a continuous channel extending about the mold roll and positioned such that the resin only partially fills the channel, thereby forming in the channel a raised portion of the selvedge region in which the resin layer is of a greater thickness than at a point between the array and the raised portion.

2. The method of claim 1, wherein the pressure is applied in a nip between the mold roll and a counter-rotating pressure roll.

3. The method of claim 1, wherein the layer edge is formed within the channel.

4. The method of claim 3, wherein the layer edge is formed against an axially distal wall defining the channel.

5. The method of claim 1, wherein the channel is defined between straight, parallel walls.

6. The method of claim 1, wherein the channel has a depth, measured in a radial mold roll direction from the outer surface of the mold roll adjacent the channel, that is between about 20 and 35 percent of a width of the channel, measured along a rotational axis of the mold roll.

7. The method of claim 1, wherein the channel is of constant cross-sectional area about the mold roll.

8. The method of claim 1, wherein the mold roll cavities closest to the channel are spaced from a near edge of the channel a distance less than 0.8 times a width of the channel, measured along a rotational axis of the mold roll.

9. The method of claim 1, wherein the substrate is porous and the flowable resin is pressed into pores of the substrate while the resin is carried on the mold roll.

10. The method of claim 9, wherein the substrate surface is fibrous and the pores comprise spaces between substrate fibers.

11. The method of claim 9, wherein the substrate surface is of a topography that undulates across the surface, the layer edge traversing undulations of the surface.

12. The method of claim 9, wherein the resin is pressed into the substrate pores under the pressure applied to fill the cavities.

13. The method of claim 1, wherein the layer of resin is of a thickness in the raised portion that is between about two and four times a thickness of the layer at a point between the array and the raised portion.

14. The method of claim 1, wherein the channel has a bottom with a chamfered or rounded edge.

15. The method of claim 1, wherein the channel follows a serpentine path about the mold roll.

16. The method of claim 1, wherein the mold roll defines grooves immediately outboard of the channels and forming an outboard side of each channel, and wherein ribs are disposed in the grooves during application of the pressure and impede lateral flow of the flowable resin.

17. The method of claim 16, further comprising trimming flash from the grooves after the application of pressure and before laminating to the flexible substrate.

18. The method of claim 1, further comprising, after the application of pressure and before laminating to the flexible substrate, applying heat to an exposed surface of the resin layer while the resin layer is carried on the mold roll.

19. The method of claim 1, wherein the channel has a depth that is less than a depth of the cavities.

20. A method of making a laminated touch fastener, the method comprising:
    introducing flowable resin to a limited circumferential band of an outer surface of a rotating mold roll defining an array of cavities extending inward from an outer surface of the mold roll within the band, and defining grooves on either side of the circumferential band;
    positioning the mold roll in cooperation with a pressure applicator, with ribs of the pressure applicator positioned in the grooves of the rotating mold roll to laterally bound the circumferential band and, with the ribs positioned in the groove, applying pressure to the resin to fill the cavities with resin and form a layer of the applied resin interconnecting projections molded within the cavities and extending across the circumferential band between the ribs;
    carrying the layer of resin on the mold roll to a position in the rotation of the mold roll where the grooves are free of the ribs; and then
    laminating the layer of resin to a flexible substrate while the layer of resin is carried on the mold roll, the substrate being of greater width than the layer of resin, thereby forming a laterally bounded layer of resin from which the molded projections extend, the bounded layer laminated to the substrate and having at least one layer edge adjacent an exposed region of the substrate.

21. The method of claim 20, further comprising trimming flash from the grooves after the application of pressure and before laminating to the flexible substrate.

22. The method of claim 20, further comprising, after the application of pressure and before laminating to the flexible substrate, applying heat to an exposed surface of the resin layer while the resin layer is carried on the mold roll.

23. A method of making a laminated touch fastener, the method comprising:
    introducing flowable resin to a limited region of an outer surface of a rotating mold roll defining an array of cavities extending inward from an outer surface of the mold roll;
    applying pressure to the resin to fill the cavities with resin and form a layer of the applied resin interconnecting projections molded within the cavities; and
    laminating the layer of resin to a flexible substrate while the layer of resin is carried on the mold roll, the substrate being of greater width than the layer of resin, thereby forming a laterally bounded layer of resin from which the molded projections extend, the bounded layer laminated to the substrate and having at least one layer edge adjacent an exposed region of the substrate, the layer having a selvedge region void of the molded projections and defined between the projections and the layer edge;
    wherein the mold roll defines a continuous channel extending about the mold roll and positioned such that the resin at least partially fills the channel, thereby forming in the channel a raised portion of the selvedge region in which the resin layer is of a greater thickness than at a point between the array and the raised portion;
    wherein the mold roll defines grooves immediately outboard of the channels and forming an outboard side of each channel, and wherein ribs are disposed in the grooves during application of the pressure and impede lateral flow of the flowable resin.

24. The method of claim 23, further comprising trimming flash from the grooves after the application of pressure and before laminating to the flexible substrate.

* * * * *